United States Patent [19]
Mierendorf et al.

[11] Patent Number: 5,464,745
[45] Date of Patent: Nov. 7, 1995

[54] PROTEIN LIGAND BINDING REGION MAPPING SYSTEM

[75] Inventors: Robert Mierendorf, Madison, Wis.; Richard Garber, Seattle, Wash.; Robert Novy, Verona, Wis.; Beth Hammer, Madison, Wis.

[73] Assignee: Novagen, Inc., Madison, Wis.

[21] Appl. No.: 40,753

[22] Filed: Mar. 31, 1993

[51] Int. Cl.$^6$ .............................. C12Q 1/68; C12N 15/63; C12P 21/00

[52] U.S. Cl. ............................. 435/6; 435/7.1; 435/91.41; 435/172.3; 435/69.1; 435/320.1; 435/252.3; 935/77; 935/23; 935/79; 935/80; 436/501

[58] Field of Search .......................... 435/6, 5, 7.1, 7.72, 435/172.3, 194, 320.1, 252.3, 91.4, 91.41, 69.1; 935/77, 78, 79; 436/501, 86

[56] References Cited

U.S. PATENT DOCUMENTS

| | | | |
|---|---|---|---|
| 4,952,496 | 8/1990 | Studier et al. | 435/91 |
| 4,985,359 | 1/1991 | Oberbaumer | 435/172.3 |

OTHER PUBLICATIONS

Clark, J. Nucleic Acid Res. (1988) 16:9677–9686.
Bahou et al. J. Clin. Invest (1989) 84:56–61.
Dowbenko et al. J. Virol. (1988) 62:4703–4711.
NovaTope System Manual (1992) pp. 1–16.
Carballeira et al. BioTechniques (1990) 9:276–281.
Mierendorf et al. Methods in Enzymology (1987) 152:458–469.
Myers et al. Biochemistry (1991) 30:7661–7672.
Gubler et al. Gene (1983) 25:263–269.
Baehringer Mannheim Catalog (1990/1991) pp. 67, 30, 31, 38.
Novagen Technical Bulletin No. 56 (Oct. 27, 1992).
Novagen advertisement "A Revolutionary Method for Rapid Epitope Mapping," *BioTechniques* Nov. 13, No. 5 (Nov. 1992).
Anderson, Stephen, "Shotgun DNA sequencing using cloned DNase I–generated fragments," *Nucleic Acids Research* vol. 9, No. 13:3015–3027 (1981).
Cwirla, et al., "Peptides on phage: A vast library of peptides for identifying ligands," *Proc. Natl. Acad. Sci. USA* 87:6378–6382 (1990).
Devlin, et al., "Random Peptide Libraries: A Source of Specific Protein Binding Molecules," *Science* 249:404–406 (1990).
NovaTope™ System Manual, Nov. 7, 1992.
Scott, Jamie K. and George P. Smith, "Searching for Peptide Ligands with an Epitope Library," *Science* 249:386–390 (1990).
Smith, George P., "Filamentous Fusion Phage: Novel Expression Vectors That Display Cloned Antigens on the Virion Surface," Abstract, Division of Biological Sciences, University of Missouri (1985).

*Primary Examiner*—Margaret Parr
*Assistant Examiner*—Carla Myers
*Attorney, Agent, or Firm*—Quarles & Brady

[57] ABSTRACT

A method for determining the nucleic acid sequence that encodes ligand binding domain on any protein encoded by a known gene includes the steps of non-specifically cleaving the coding region of the known gene, size-selecting the cleavage products, cloning the size-selected gene products into an expression vector active in a heterologous host, using a novel cloning strategy expressing the peptides produced by the clones and screening for clones that produce peptides that interact with an antibody or ligand of interest.

10 Claims, 1 Drawing Sheet

5,464,745

PROTEIN LIGAND BINDING REGION MAPPING SYSTEM

FIELD OF THE INVENTION

This invention relates to the broad field of protein analysis, and particularly to the field of determining nucleic acid sequences that encode protein ligand binding regions recognized by antibodies or other ligands.

BACKGROUND OF THE INVENTION

One of the continuing objectives of molecular biology research is to clone genes for proteins and then to characterize the domains and activities in the proteins. Generally if one has an antibody that recognizes a protein of interest, or a ligand to which the protein binds, it is possible to isolate and to purify the gene which encodes the protein of interest. Several techniques exist for using antibodies to screen proteins encoded by cloned DNA insert libraries in plasmid or phage expression vectors in a host. Foreign proteins encoded by the cloned DNA are accessible to the known antibody or ligand and, for example, may be separated from a population of uninteresting insert-containing phage using standard affinity techniques, such as chromatography with bound antibody or ligand. Using such screening techniques, one may isolate the bacterial clones which contain the gene of interest and may then undertake a wide array of molecular biological analyses of that gene.

At a finer scale, it is often useful to determine which amino acid sequences of a protein bind to a ligand or known antibody. Such sequences are referred to here as ligand binding domains and include antigenic determinants, or epitopes, as well as domains that bind to biological receptors. A ligand binding domain is a three-dimensional region of a protein molecule whose ability to bind a ligand or antibody is a function of three attributes. Of foremost importance is the linear sequence of amino acids that form the ligand binding domain of the protein. Secondly, the proper folding and twisting of a linear amino acid chain into a three-dimensional structure can form a ligand binding domain. Finally, ligand binding domains may form in crevices created during the interaction of several amino acid chains in a multi-chain protein.

One method for determining a priori which amino acid sequences form ligand binding domains is to use the antibody or ligand of interest to challenge a library of short amino acid sequences expressed as a peptide in a host cell. Along these lines, in efforts to generate diverse epitope libraries, collections of synthetic oligonucleotides encoding all possible hexapeptides (6-mers) and decapentapeptides (15-mers) have been produced and cloned into gene III of filamentous bacteriophage expression vectors such as FUSE5, M13LP67 and fAFF1. Gene III encodes pIII, a minor virion coat protein which tolerates short insertions between its internal structural domain and its external functional domain. See Scott, J. K. and G. P. Smith, "Searching for Peptide Ligands with an Epitope Library," 249 *Science* 386–390 (1990), Devlin, J. J. et al., "Random Peptide Libraries: A Source of Specific Protein Binding Molecules," 249 *Science* 404–406 (1990), and Cwirla, S. E., et al., Peptides on Phage: A vast library of peptides for identifying ligands," 87 P.N.A.S. 6378–6382 (1990). One may identify bacterial clones having a phage that encodes antibody- or ligand-binding peptides by selecting nitrocellulose-bound bacterial colonies with antibody- or ligand-binding affinity. The DNA sequence encoding the selected peptide or peptides can then easily be determined by standard DNA sequencing techniques.

Of course, mere binding of a hexapeptide to an antibody does not guarantee that the naturally-occurring epitope is identical or even related to the short peptide. For that reason, such synthetic epitopes are often referred to as mimetopes because they merely mimic the behavior of natural epitopes. While epitopes isolated in this manner may prove useful in the development of synthetic drugs and the like, they do not necessarily help a researcher discover epitope sites on genuine proteins of interest. The random oligonucleotide approach is further limited by the fact that naturally occurring ligand binding domains may be longer than fifteen amino acids long. As the length of the tested sequence increases, the number of possible epitopes increases exponentially. For instance, there are approximately $4\times10^7$ different hexapeptide epitopes and $3\times10^{19}$ possible 15-residue peptides. In general, the present practical limit on the creation and screening of random octapeptide libraries is a library containing approximately $2.5\times10^{10}$ clones. For representative libraries of still longer test sequences, the ability to generate and screen libraries having sufficient numbers of distinct insert-containing clones becomes an issue if the desired ligand binding domain is longer than just a few amino acids. It is also time consuming and expensive to generate very long oligonucleotides. Furthermore, since binding sites are not necessarily encoded by contiguous bases, it may be important to consider longer peptides when searching for these ligand binding sites.

Determining the location of a ligand binding domain on a protein has often been a difficult undertaking. Typically, one would express and test deletion mutants of cloned genes for loss of activity such as antibody binding or enzymatic function. After broadly localizing a binding site to a particular domain, it would be necessary to chemically synthesize individual peptides from that protein domain, and to further demonstrate binding of a synthesized peptide to the antibody or ligand of interest. Furthermore, construction of deletion mutants has frequently required the presence of advantageous restriction enzyme sites within the protein coding region. However, when preparing deletion mutants by removing restriction enzyme fragments, one always risks cleaving a ligand binding site in two in the process.

Other methods used have involved cleavage of purified proteins into constituent peptides by protease digestion, and then determining the ligand binding region by immunological assay of the protease digestion products. This approach is extremely time consuming and has two major disadvantages. One disadvantage is that the cleavage of the protein is often incomplete and difficult to control so that the fragments are irregular. A second problem is that when the target epitope is identified, the amount of peptide available, which must be isolated, purified, and sequenced to obtain useful information, can be extremely small.

In summary, then, while it is possible to isolate genes using antibodies directed to a gene product, and to ask a priori which short amino acid sequence binds a known antibody or ligand, no existing convenient system permits one to quickly and easily determine which amino acids on a known protein of interest are antigenic or which nucleotide bases on a gene of interest encode a ligand binding site. No convenient systematic approach exists for routinely producing peptide libraries from all regions of a known protein-encoding gene. Typically, peptide analysis of known coding regions is performed by chemically synthesizing individual peptides, an expensive and time consuming task. As a result, detailed peptide analysis of entire coding regions has been limited to a few proteins of major economic importance, such as insulin. What is desired is a system that permits rapid subcloning of entire protein coding regions for subsequent fine-scale mapping of amino acids that encode ligand binding domains.

SUMMARY OF THE INVENTION

The present invention is summarized in that a peptide library of short, protein-encoding fragments of a complete gene coding region having a wide variety of lengths and endpoints is formed by non-specific digestion of a cloned coding region into fragments of many sizes followed by insertion of the fragments into a high efficiency expression vector by means of a novel cloning strategy. The novel cloning strategy entails the enzymatic addition of complementary single nucleotide overhangs on fragments and vector. The library of recombinants are then transformed into competent bacterial host cells which are plated and screened for colonies expressing peptides that form the desired epitope. After purification and confirmation of epitope-producing clones, the peptide may be overproduced and purified for further analysis. In addition, the nucleic acid sequence encoding that peptide may be determined to pinpoint the cloned portion of the gene of interest that encodes the epitope.

It is an object of the present invention to provide a kit useful for determining which regions of a gene of interest encode epitopes specific to an antibody known to recognize the product of the gene of interest.

It is another object of the present invention to provide a method generating peptide-encoding sub-clones of a gene of interest in an expression vector.

It is an advantage of the present invention that the sub-cloning strategy prevents recircularization of the vector, eliminates tandem insertions, and eliminates the need for special linkers and additional fractionation steps.

Other features, objects, and advantages of the present invention will become apparent when considered in light of the following specification.

DETAILED DESCRIPTION OF THE INVENTION

Figure 1:
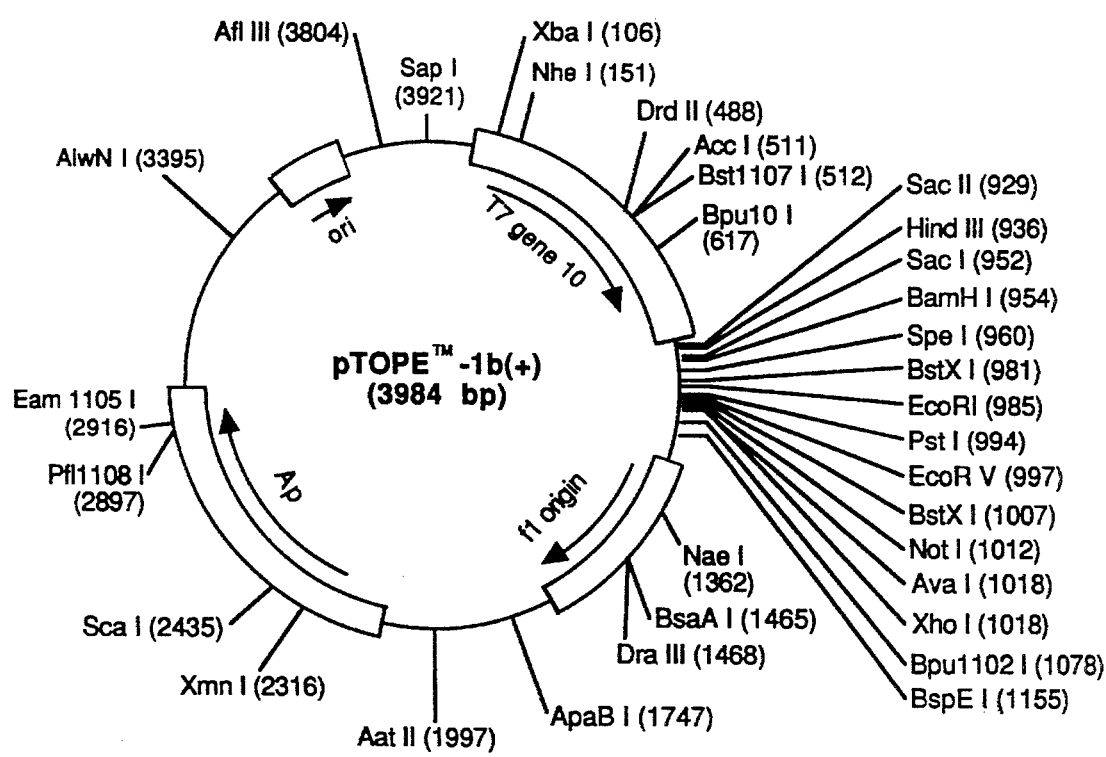
FIG. 1 is a map of pTOPE-1b(+) the sequence of which is attached as SEQ ID: 1. pTOPE-1b(+) is a plasmid vector useful in the method for mapping the ligand binding domains of a protein.

All proteins that interact with other molecules, including enzymes, substrates, nucleic acids, or other proteins, interact with those other molecules at discrete sites on the protein known as ligand binding domains. A ligand binding domain may be a site into which another molecule fits via optimal hydrogen bonding distances, hydrophobic interactions, Van der Waals forces, or ionic interactions. Ligand binding domains are determined, in large part, by the amino acid sequence at the epitope site. The amino acid sequence itself determines the folding pattern of the protein chain, as amino acids of various charge and dimension attract or repel each other in roughly predictable, but far from certain, ways. Furthermore, separate independent amino acid chains often join together to form complete proteins, with the ligand binding domains influenced by neighboring chains. A specific useful class of ligand binding domains are epitopes, or antigenic determinants, which are the portions of proteins recognized by antibodies.

By using the present invention, one can easily generate a population of overlapping clones that each encode peptides of approximately 15 to 50 amino acids or more from a section of the protein of interest. The non-specific cleavages in the gene of interest allow the cloning of many more potential ligand binding domain encoding peptides than one could clone easily using discrete restriction enzyme fragments. As a result, the likelihood of capturing an entire ligand binding domain in a single peptide is increased over existing techniques.

The gene of interest may be any DNA form of a gene that encodes a protein of interest, though preferably if the gene is eukaryotic, the gene would be a cDNA copy of an mRNA. The reason for the preference is that cDNA contains no introns; instead, the cDNA reflects the spliced coding region of a gene. If the gene of interest were to contain introns, the library constructed might contain a high background of non-coding DNA fragments which would not reflect the amino acid sequence of, and which would not form binding sites like, the native protein. This reduces the efficiency of the search for ligand binding site fragments. For this reason, cDNA clones of eukaryotic genes are preferred.

To produce overlapping fragments of the coding region of the gene of interest, the coding region of the gene is non-specifically cleaved by a non-sequence specific cleavage agent, such as DNase I in the presence of $Mn^{2+}$, causing double stranded cleavage of the DNA molecule. By varying the concentration or digestion time of DNase I, or other cleavage agent, the average size of DNA fragments produced during digestion can be controlled. Subsequent examination of products of each digestion will indicate the range of fragment sizes in each digestion. The present inventors have demonstrated that a mix of fragments ranging from about 30 to 150 base pairs in size, and typically smaller than about 250 base pairs are stably expressed at high levels in host cells without inhibiting expression of the larger fusion protein. The exact length of individual fragments is not critical. However, by including randomly digested fragments of varying length in the library, one may determine the minimal epitope size by comparing the activities of overlapping clones and determining which nucleotides are essential for encoding a particular epitope. The average length of an epitope is approximately 5–10 amino acids long.

Although DNase I is a preferred enzyme for randomly digesting the gene of interest, other methods for generating overlapping subclones of the gene are also possible. For example, other non-sequence-specific endonucleases (i.e. which digest DNA randomly or pseudorandomly) may be used under conditions appropriate for double-stranded digestion. Other such possible random cleavage agents include sonication of the DNA and cleavage with a restriction enzyme which is a frequent pseudorandom cutter (e.g. CviJ I, a "two-base" cutter). Non-enzymatic processes, such as mechanical disruption or sonication that cleave DNA molecules without specificity could be used to form fragments of random length. Alternatively, appropriate pairs of site-specific restriction enzymes cutting at common sites may also be used to generate overlapping clones. In such a case, it is important to remember that the reading frame of the peptide expression vector must be maintained when cloning the cut site into the vector. It should be noted however, that random fragment generation using DNase I or similar nuclease is preferable because of the risk that restriction enzyme sites will disrupt the binding site encoding region of the DNA. Such a risk is absent when using randomly-digested DNA because fragments having a 5' end at each sequence position are represented in the library.

To ensure a fragment size distribution appropriate for forming peptides averaging 15–50 amino acids long, the digestion products were fractionated by electrophoresis on a polyacrylamide or agarose gel alongside DNA fragment size markers. Alternatively, other size-separating techniques such as HPLC or FPLC might be made to work.

After the size-fractionated fragments of average size ranging from about 50 to 150 base pairs are eluted and purified from the agarose or other separation medium, the ends of fragments must be made blunt-ended. This may be accomplished by adding complementary bases to any 5' terminal overhanging strand ends or by removing 3' overhanging bases. A preferred method for ensuring blunt ends is to use T4 DNA polymerase to both fill in the complements to the 5' overhanging bases and remove 3' overhanging bases by virtue of its 3'→5' exonuclease activity. If the cleavage method results in double stranded and blunt ended DNA fragments, this step may be unnecessary.

The blunt-ended DNA fragments are then treated with Tth DNA polymerase in the presence of dATP, which adds a single dA residue to each 3' end. This creates a single base d(A) overhang on each 3' end of the DNA fragments, useful in subsequent cloning. This single base overhang is of particular importance in the overall process. This overhang not only allows for convenient insertion into the expression vector, it ensures that tandem combinations of the DNA fragments cannot be created.

The purified fragments were cloned into a plasmid expression vector functional in prokaryotic cells. A convenient plasmid vector is pTOPE-1b(+), which includes the necessary signals for transcription from a T7 RNA polymerase promoter, a prokaryotic ribosome binding site, an antibiotic resistance gene and a transcription terminator. A restriction map of the circular pTOPE-1b(+) plasmid is depicted in FIG. 1. The nucleotide sequence of pTOPE-1b(+) is attached as SEQ ID:1. In SEQ ID:2, the fusion protein encoded by pTOPE-1b(+) is set forth. This plasmid includes, following the T7 promoter, a protein coding leader sequence from gene 10 from T7 so that the proteins created by it will be fusions of the gene 10 leader to the proteins encoded by the DNA fragments. Between the gene 10 DNA and the insert DNA may be several nucleotides that are part of the multiple cloning site and encode amino acids in the peptide produced from the vector. The gene 10 leader provides for stable high levels of expression and actuates the accumulation of the fusion protein as inclusion bodies in the host protected from potential protease degradation. The plasmid is a high copy number version of the pBR322-derivative plasmid pET-17× b, which contains a pUC origin of replication. Many other vectors comprising a promoter, a terminator and selectable marker gene and capable of directing expression of an inserted gene or gene fragment are known to the art. One would be free to choose any vector functional in the desired host cell when practicing this invention.

To prepare for cloning, pTOPE-1b(+) was linearized by digestion with EcoR V, to generate a blunt-end cut downstream from the T7 promoter and was treated with Taq DNA polymerase in the presence of dTTP to add single 3' dT overhangs. This resulted in a vector with ends complementary to the single dA overhangs on the fragments to be cloned. Such ends could equally well be generated by cleavage of the vector with a restriction enzyme which leaves appropriate single 3' overhangs.

The choice of complementary single nucleotide 3' overhangs when preparing vector and insert for ligation is an important feature of this method, though the nucleotides need not be dA and dT. The other complementary nucleotides, dC and dG, would also work. The advantage of the dA is that it takes advantage of the natural tendency of Tth DNA polymerase to add dA's preferentially. If other bases were added instead, an additional purification step after the blunt ending would be required. The novel cloning strategy based on these single nucleotide overhangs has several advantages including the prevention of tandem inserts, the drastic reduction of background colonies without inserts, and eliminating the need for special linkers and additional fractionation steps. Thus the overall procedure becomes more convenient and less likely to suffer from losses that would occur if more manipulation and additional fractionation steps were required.

After ligating the putative binding site-encoding sequence fragments into an expression vector using standard ligation techniques, ligation mixes may be transformed into competent hosts and plated on selective media. Antibiotic resistant colonies may be grown to approximately 1–2 mm diameter. Although the utility of this invention has been demonstrated in bacteria, it is equally useful in other host cell types such as plants or animal cells. Fragments of a gene of interest may be cloned into vectors functional in plant or animal cells and having appropriate regulatory elements. Recombinant vectors may then be transferred into such cells by transfection, cell fusion, electroporation, particle acceleration or any other method for introducing foreign genes into heterologous hosts.

Because the pTOPE-1b(+) vector used by the present inventors carried the T7 RNA polymerase-binding promoter in addition to an antibiotic selection gene, useful hosts include lambda DE3 bacterial lysogens. Lambda DE3 lysogens carry the T7 RNA polymerase gene under the control of a lacUV5 promoter. Because the host constitutively produces a low level of T7 RNA polymerase, the cloned DNA fragments are expressed as peptides since they are inserted downstream of the strong T7 promoter. Other hosts containing the T7 RNA polymerase gene and sensitive to the antibiotic resistance encoded on the vector would be appropriate hosts for the vector used by the present inventors. Similarly, if the vector included a different promoter active in bacterial cells, the host should preferably provide the appropriate RNA polymerase constitutively. Alternatively, inducible promoters could also be used in which transcription is effected by IPTG (lac,tac), heat ($\lambda P_L$/cI857) or other control mechanisms.

To determine which bacterial colonies produced ligand binding-containing peptides, abbreviated colony lift assays may be performed on each plate of colonies by overlaying each with a nitrocellulose filter and then lysing the bacterial cells, retaining the protein extract of each colony in situ on the nitrocellulose filter. After washing each filter in a detergent solution, the filters can be incubated with antibody probes directed against the protein of interest. If the fusion protein produced by any colony forms a conformationally correct epitope, the antibody probe will bind to that segment or epitope.

After washing away unbound epitope-directed antibody, the filters can be incubated with a species-specific secondary antibody conjugated to a molecule, such as an enzyme, whose presence can be detected by colorimetric assay. For example, to detect mouse monoclonal IgG antibodies, a goat anti-mouse IgG-alkaline phosphatase conjugate may be used. The antibody portion of the molecule may be goat anti-rabbit IgG, if the epitope-directed antibody was made in a rabbit; goat anti-rat IgG, if the epitope-directed antibody was made in a rat, or goat anti-human, if the primary antibody was isolated from a human. The goat anti-mouse IgG portion of the conjugate will bind tightly to any IgG antibody probes still bound to protein deposited on the nitrocellulose. The alkaline phosphatase portion of the conjugate can be revealed by incubation with the color development substrates 5-bromo-4-chloro-3-indolylphosphate (BCIP) and nitroblue tetrazolium (NBT). Dark blue positive colony signals will appear within minutes.

Colonies corresponding to the positive signals on the nitrocellulose filters can be picked, streaked onto selective plates, and rescreened the following day according to the above screening procedure. Colonies surviving a second screen were presumed to contain plasmid inserts capable of encoding a small peptide that could bind to the antibody, or other ligand used in the screening.

Using a standard method for growing bacterial colonies and isolating plasmid DNA, positive colonies can be grown and plasmid DNA was isolated. To determine which portion of the coding region was inserted into the plasmid vector in each colony, isolated plasmid DNA can be sequenced after alkali denaturation by the dideoxy chain termination method, as described in Mierendorf and Pfeffer, 152 Methods Enzymol. 556–562 (1987) using T7 DNA polymerase with T7 gene 10 and T7 terminator primers. Alternatively, any of the several other methods for determining the DNA sequence of a plasmid insert, such as standard dideoxy chain termination sequencing or PCR based sequencing, could be used. By sequencing several clones, a series of overlapping sequences should be obtained which encode the relevant binding domain. The minimal sequence necessary for binding can be determined by finding the minimum sequence held in common among all of the positive clones.

This screening can be accomplished with other non-antibody ligands whose presence can be detected by an assay system. For instance, a fluorescent or radiolabeled ligand, or a ligand bound to a molecule detectable by colorimetric assay would be equally useful for identifying ligand binding site-containing colonies. Additionally, any molecule which binds to a cellular receptor, or which is itself a receptor for a molecule can function as a ligand within the scope of the present invention. Such molecules include, but are not limited to, the human HLA and murine H-2 antigens, growth factors, growth factor receptors, T-cell receptors, hormone receptors and transcription factors. In short, the method described here is useful for characterizing a wide variety of ligand binding domains and epitopes in any protein of interest.

EXAMPLES

Construction of Epitope Mapping Library

Plasmid DNA copies containing a gene of interest such as E. coli beta-galactosidase and human p53 were purified using standard plasmid DNA purification techniques and digested with various amounts of DNase I (United States Biochemical Corp.) using the dilutions shown in Table I.

TABLE I

| Sample # | 10X buffer | 10X MnCl$_2$ | DNA | DNase I/ dilution | sterile deionized water |
|---|---|---|---|---|---|
| 1 | 3 µl | 3 µl | 30 µg | 3 µgl 1:140 | to 30 µl |

TABLE I-continued

| Sample # | 10X buffer | 10X MnCl$_2$ | DNA | DNase I/ dilution | sterile deionized water |
|---|---|---|---|---|---|
| 2 | 3 µl | 3 µl | 30 µg | 3 µl 1:200 | to 30 µl |
| 3 | 3 µl | 3 µl | 30 µg | 3 µl 1:300 | to 30 µl |
| 4 | 3 µl | 3 µl | 30 µg | 3 µl 1:450 | to 30 µl |

DNase I, stored in 50% glycerol at a concentration of 2.6 units/ml at −20° C. was prepared for use by diluting the concentrated enzyme stock into 1 X reaction buffer immediately before use to the dilutions noted in Table I. Samples 1 through 4 containing decreasing concentrations of DNase I were incubated for 10 minutes at 21° C. and were stopped by the addition of 1.5 µl 0.5M EDTA. 1 µl of each sample was analyzed by electrophoresis on a 2% agarose (GTG grade, FMC Corp.) gel containing 0.5 micrograms/ml ethidium bromide in TAE buffer (1×is 40 mM Tris-acetate pH8.5, 2 mM EDTA) using standard methods. Appropriate DNA size markers (BioMarker low, BioVentures, Inc.) were run in an adjacent lane. The digestion which produced DNA fragments in the 50 to 150 base pair size range was used for further purification.

To purify the DNA fragments from the DNase I reaction mix, the remainder of the reaction mix was loaded onto a 0.5 cm wide slot of a 2% agarose gel prepared as described above and run until the desired DNA fragments were sufficiently resolved. A gel slice containing fragments ranging in size from approximately 50 to approximately 150 base pairs as measured by DNA fragment size markers was excised. The fragments contained in the excised gel slice was eluted using an Elutrap (Schleicher and Schuell) apparatus according to the manufacturer's instructions. The DNA eluted from the Elutrap in a volume of about one ml and was extracted once with 1 ml of TE-buffered phenol: CIAA (1:1) and then once with 1 ml CIAA (chloroform:isoamyl alcohol, 24:1). DNA fragments were precipitated after phenol extraction by adding 0.1 volume of 3M sodium acetate and 2 volumes of ethanol followed by storage at 0° C. for 1 hour. Precipitated DNA fragments were collected by centrifugation at 12000× g for 15 minutes after which, the DNA pellet was rinsed with 70% ethanol, dried in air, and resuspended in 50 µl TE buffer (10 mM Tris-HCl pH 8.0, 1 mM EDTA). The concentration of DNA recovered was determined spectrophotometrically by absorbance at 260 nm.

To prepare the DNA fragments for cloning into the expression vector, the fragments were treated with T4 DNA polymerase to make flush any remaining sticky ends following DNase I digestion. The reactions included 1 microgram of DNA fragments in TE buffer, 50 mM Tris-HCl pH 8, 5 mM DTT, 50 µg/ml bovine serum albumin, 5 mM MgCl$_2$, 100 µM each of dATP, dGTP, dCTP, dTTP (Pharmacia), and 5 U of T4 DNA polymerase (New EnglandBiolabs) in sterile deionized water to 25 µl. The polymerase reaction was incubated at 11° C. for 20 minutes. The enzyme was then inactivated at 75° C. for 10 minutes.

Single dA residues were added to the 3' ends of each strand by adding the following to the above reaction: 8.5 µl of 10 X dA addition buffer (100 mM Tris-HCl pH 9.0, 500 mM KCl, 0.1% gelatin, 1.0% Triton X-100), 17 µl 1 mM dATP (Pharmacia), 34 µl sterile deionized water, 0.5 µl (1.5 U) Tth DNA polymerase (Molecular Biology Resources). The addition of dA was initially performed at 70° C. for 2 hours, without inactivation except for that caused by the freeze/thaw cycling. Later this step was altered so that the dA addition took place over 15 minutes at 70° C. followed by extraction with one volume of CIAA to inactivate the enzyme.

Separately, EcoR V-digested pTOPE-1b(+) vector DNA was prepared for ligation to the DNA fragments containing single 3' dA residues. Since EcoR V cuts leaving blunt ends, it was necessary to add a residue complementary to the 3' dA ends of the inserts. To do so, the linearized vector was treated with Taq DNA polymerase in the presence of dTTP to yield linearized vector with single dT additions at the 3' end of each strand.

Vector and fragments were ligated together by adding approximately 0.2 pmol of DNA fragments from the dA-addition reaction to 0.04 pmol of the linearized pTOPE-1b(+) vector with 3' dT overhangs in a buffer which included 20 mM Tris-HCl pH 7.6, 5 mM MgCl$_2$, 5 mM dTT, and 50 µg/ml nuclease-free BSA. The ligation was accomplished by adding 200 cohesive end units of T4 DNA ligase (New England Biolabs) and 0.5 µl 10 mMATP. The reaction was performed in a total volume of 10 µl with the difference made up of sterile deionized water. The ligation proceeded at 16° C. for 2 hours and 1 µl was then used directly to transform competent *E. coli* cells. Four lambda DE3 lysogens have been used as a source of competent cells with similar results. The 4 strains are NovaBlue(DE3), NovaBlue(DE3)pLysS, BL26(DE3)pLysS, and BL21(DE3)pLysS. These bacterial cells were made competent for transformation according to the published procedures of Sambrook et al., Molecular Cloning, a laboratory manual, second edition, Cold Spring Harbor Laboratory Press (1989) and Novagen Technical Bulletin No. 55. After transformation, the cells were plated on LB agar plates containing 50 µg/ml carbenicillin plus 34 µg/ml chloramphenicol as selection agents (except for NovaBlue (DE3) where only carbenicillin was used).

EXAMPLE 2

Screening Transformants for Epitope-Encoding Inserts

Several thousand antibiotic-resistant colonies per 85 mm plate grew overnight at 37° C. to a colony size of 1–2 mm diameter. The plates were chilled at 4° C. for 30 minutes and were then overlaid with a nitrocellulose filter disk (Schleicher and Schuell BA85) The filters were incubated on the plates for 1 minute, were removed, and were placed colony side up on Whatman 3 MM paper saturated with 20 mM Tris-HCl pH 7.9, 6M urea, 0.5M NaCl for 15 minutes at room temperature. The NovaBlue (DE3) colonies were exposed to chloroform vapor for 15 minutes. The filters were then immersed in TNT +1% gelatin for 15 minutes with gentle agitation to saturate non-specific protein binding sites. TNT is 10 mM Tris-HCl pH 8.0, 150 mM NaCl, 0.05% Tween-20. After two 15 minute washes with TNT, the filters were incubated with TNT-diluted mouse antibody probes known to recognize the protein encoded by the gene of interest for 30 minutes with agitation. The filters were then washed 3 times for 10 minutes with TNT and were then incubated with goat anti-mouse IgG alkaline phosphatase conjugate (Jackson ImmunoResearch Laboratories) diluted 1:5000 in TNT for 30 minutes. Following three more 10 minute washes in TNT, the filters were incubated in alkaline phosphatase buffer containing color development substrates BCIP and NBT, to a final concentration of BCIP at 168 µg/ml and NBT at 332 µg/ml. Dark blue positive colony signals appeared within 5 minutes. Colonies corresponding to the positive signals were picked, were streaked on selective plates, and were rescreened the following day according to the above procedure.

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3984 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: pTOPE-1b(+)

( i x ) FEATURE:
        ( A ) NAME/KEY: promoter
        ( B ) LOCATION: 67..85
        ( D ) OTHER INFORMATION: /function="T7 Promoter"

( i x ) FEATURE:
        ( A ) NAME/KEY: RBS
        ( B ) LOCATION: 134..139

( i x ) FEATURE:

( A ) NAME/KEY: CDS
( B ) LOCATION: 148..1092
( D ) OTHER INFORMATION: /product="5'end of T7 gene 10 fusion protein"/note="This coding region is interrupted during cloning by insertion of putative epitope encoding DNA."

( x i ) SEQUENCE DESCRIPTION: SEQ ID NO:1:

| | | | | | | | | | | | | |
|---|---|---|---|---|---|---|---|---|---|---|---|---|
| CCCGGTACC | CATAACTTCG | TATAGCATAC | ATTATACGAA | GTTATGGGGA | TCTCGATCCC | | | | | | | 60 |
| GCGAAATTAA | TACGACTCAC | TATAGGGAGA | CCACAACGGT | TTCCCTCTAG | AAATAATTTT | | | | | | | 20 |

| GTTTAACTTT | AAGAAGGAGA | TATACAT | ATG | GCT | AGC | ATG | ACT | GGT | GGA | CAG | 71 |
|---|---|---|---|---|---|---|---|---|---|---|---|
| | | | Met | Ala | Ser | Met | Thr | Gly | Gly | Gln | |
| | | | 1 | | | | 5 | | | | |

| CAA | ATG | GGT | ACT | AAC | CAA | GGT | AAA | GGT | GTA | GTT | GCT | GCT | GGA | GAT | AAA | 19 |
|---|---|---|---|---|---|---|---|---|---|---|---|---|---|---|---|---|
| Gln | Met | Gly | Thr | Asn | Gln | Gly | Lys | Gly | Val | Val | Ala | Ala | Gly | Asp | Lys | |
| | 10 | | | | | 15 | | | | | 20 | | | | | |

| CTG | GCG | TTG | TTC | TTG | AAG | GTA | TTT | GGC | GGT | GAA | GTC | CTG | ACT | GCG | TTC | 267 |
|---|---|---|---|---|---|---|---|---|---|---|---|---|---|---|---|---|
| Leu | Ala | Leu | Phe | Leu | Lys | Val | Phe | Gly | Gly | Glu | Val | Leu | Thr | Ala | Phe | |
| 25 | | | | | 30 | | | | | 35 | | | | | 40 | |

| GCT | CGT | ACC | TCC | GTG | ACC | ACT | TCT | CGC | CAC | ATG | GTA | CGT | TCC | ATC | TCC | 315 |
|---|---|---|---|---|---|---|---|---|---|---|---|---|---|---|---|---|
| Ala | Arg | Thr | Ser | Val | Thr | Thr | Ser | Arg | His | Met | Val | Arg | Ser | Ile | Ser | |
| | | | | 45 | | | | | 50 | | | | | 55 | | |

| AGC | GGT | AAA | TCC | GCT | CAG | TTC | CCT | GTT | CTG | GGT | CGC | ACT | CAG | GCA | GCG | 363 |
|---|---|---|---|---|---|---|---|---|---|---|---|---|---|---|---|---|
| Ser | Gly | Lys | Ser | Ala | Gln | Phe | Pro | Val | Leu | Gly | Arg | Thr | Gln | Ala | Ala | |
| | | | 60 | | | | | 65 | | | | | 70 | | | |

| TAT | CTG | GCT | CCG | GGC | GAG | AAC | CTC | GAC | GAT | AAA | CGT | AAG | GAC | ATC | AAA | 411 |
|---|---|---|---|---|---|---|---|---|---|---|---|---|---|---|---|---|
| Tyr | Leu | Ala | Pro | Gly | Glu | Asn | Leu | Asp | Asp | Lys | Arg | Lys | Asp | Ile | Lys | |
| | | 75 | | | | | 80 | | | | | 85 | | | | |

| CAC | ACC | GAG | AAG | GTA | ATC | ACC | ATT | GAC | GGT | CTC | CTG | ACG | GCT | GAC | GTT | 459 |
|---|---|---|---|---|---|---|---|---|---|---|---|---|---|---|---|---|
| His | Thr | Glu | Lys | Val | Ile | Thr | Ile | Asp | Gly | Leu | Leu | Thr | Ala | Asp | Val | |
| | | 90 | | | | | 95 | | | | | 100 | | | | |

| CTG | ATT | TAT | GAT | ATT | GAG | GAC | GCG | ATG | AAC | CAC | TAC | GAC | GTT | CGC | TCT | 507 |
|---|---|---|---|---|---|---|---|---|---|---|---|---|---|---|---|---|
| Leu | Ile | Tyr | Asp | Ile | Glu | Asp | Ala | Met | Asn | His | Tyr | Asp | Val | Arg | Ser | |
| 105 | | | | | 110 | | | | | 115 | | | | | 120 | |

| GAG | TAT | ACC | TCT | CAG | TTG | GGT | GAA | TCT | CTG | GCG | ATG | GCT | GCG | GAT | GGT | 555 |
|---|---|---|---|---|---|---|---|---|---|---|---|---|---|---|---|---|
| Glu | Tyr | Thr | Ser | Gln | Leu | Gly | Glu | Ser | Leu | Ala | Met | Ala | Ala | Asp | Gly | |
| | | | | 125 | | | | | 130 | | | | | 135 | | |

| GCG | GTT | CTG | GCT | GAG | ATT | GCC | GGT | CTG | TGT | AAC | GTG | GAA | AGC | AAA | TAT | 603 |
|---|---|---|---|---|---|---|---|---|---|---|---|---|---|---|---|---|
| Ala | Val | Leu | Ala | Glu | Ile | Ala | Gly | Leu | Cys | Asn | Val | Glu | Ser | Lys | Tyr | |
| | | | 140 | | | | | 145 | | | | | 150 | | | |

| AAT | GAG | AAC | ATC | GAG | GGC | TTA | GGT | ACT | GCT | ACC | GTA | ATT | GAG | ACC | ACT | 651 |
|---|---|---|---|---|---|---|---|---|---|---|---|---|---|---|---|---|
| Asn | Glu | Asn | Ile | Glu | Gly | Leu | Gly | Thr | Ala | Thr | Val | Ile | Glu | Thr | Thr | |
| | | 155 | | | | | 160 | | | | | 165 | | | | |

| CAG | AAC | AAG | GCC | GCA | CTT | ACC | GAC | CAA | GTT | GCG | CTG | GGT | AAG | GAG | ATT | 699 |
|---|---|---|---|---|---|---|---|---|---|---|---|---|---|---|---|---|
| Gln | Asn | Lys | Ala | Ala | Leu | Thr | Asp | Gln | Val | Ala | Leu | Gly | Lys | Glu | Ile | |
| | | 170 | | | | | 175 | | | | | 180 | | | | |

| ATT | GCG | GCT | CTG | ACT | AAG | GCT | CGT | GCG | GCT | CTG | ACC | AAG | AAC | TAT | GTT | 747 |
|---|---|---|---|---|---|---|---|---|---|---|---|---|---|---|---|---|
| Ile | Ala | Ala | Leu | Thr | Lys | Ala | Arg | Ala | Ala | Leu | Thr | Lys | Asn | Tyr | Val | |
| 185 | | | | | 190 | | | | | 195 | | | | | 200 | |

| CCG | GCT | GCT | GAC | CGT | GTG | TTC | TAC | TGT | GAC | CCA | GAT | AGC | TAC | TCT | GCG | 795 |
|---|---|---|---|---|---|---|---|---|---|---|---|---|---|---|---|---|
| Pro | Ala | Ala | Asp | Arg | Val | Phe | Tyr | Cys | Asp | Pro | Asp | Ser | Tyr | Ser | Ala | |
| | | | | 205 | | | | | 210 | | | | | 215 | | |

| ATT | CTG | GCA | GCA | CTG | ATG | CCG | AAC | GCA | GCA | AAC | TAC | GCT | GCT | CTG | ATT | 843 |
|---|---|---|---|---|---|---|---|---|---|---|---|---|---|---|---|---|
| Ile | Leu | Ala | Ala | Leu | Met | Pro | Asn | Ala | Ala | Asn | Tyr | Ala | Ala | Leu | Ile | |
| | | | 220 | | | | | 225 | | | | | 230 | | | |

| GAC | CCT | GAG | AAG | GGT | TCT | ATC | CGC | AAC | GTT | ATG | GGC | TTT | GAG | GTT | GTA | 891 |
|---|---|---|---|---|---|---|---|---|---|---|---|---|---|---|---|---|
| Asp | Pro | Glu | Lys | Gly | Ser | Ile | Arg | Asn | Val | Met | Gly | Phe | Glu | Val | Val | |
| | | 235 | | | | | 240 | | | | | 245 | | | | |

| GAA | GTT | CCG | CAC | CTC | ACC | GCT | GGT | GGT | GCT | GGT | ACC | GCG | GAT | TCA | AGC | 939 |
|---|---|---|---|---|---|---|---|---|---|---|---|---|---|---|---|---|
| Glu | Val | Pro | His | Leu | Thr | Ala | Gly | Gly | Ala | Gly | Thr | Ala | Asp | Ser | Ser | |

-continued

```
        250                        255                        260
TTG GTA CCG AGC TCG GAT CCA CTA GTA ACG GCC GCC AGT GTG CTG GAA    987
Leu Val Pro Ser Ser Asp Pro Leu Val Thr Ala Ala Ser Val Leu Glu
265                     270                 275                 280

TTC TGC AGA TAT CCA TCA CAC TGG CGG CCG CTC GAG CAG ATC CGG CTG   1035
Phe Cys Arg Tyr Pro Ser His Trp Arg Pro Leu Glu Gln Ile Arg Leu
                    285                 290                 295

CTA ACA AAG CCC GAA AGG AAG CTG AGT TGG CTG CTG CCA CCG CTG AGC   1083
Leu Thr Lys Pro Glu Arg Lys Leu Ser Trp Leu Leu Pro Pro Leu Ser
                300                 305                 310

AAT AAC TAGCATAACC CCTTGGGGCC TCTAAACGGG TCTTGAGGGG TTTTTGCTG    1139
Asn Asn
        315

AAAGGAGGAA CTATATCCGG ATAACCTGGC GTAATAGCGA AGAGGCCCGC ACCGATCGCC 1199
CTTCCCAACA GTTGCGCAGC CTGAATGGCG AATGGACGCG CCCTGTAGCG GCGCATTAAG 1259
CGCGGCGGGT GTGGTGGTTA CGCGCAGCGT GACCGCTACA CTTGCCAGCG CCCTAGCGCC 1319
CGCTCCTTTC GCTTTCTTCC CTTCCTTTCT CGCCACGTTC GCCGGCTTTC CCCGTCAAGC 1379
TCTAAATCGG GGGCTCCCTT TAGGGTTCCG ATTTAGAGCT TACGGCACC TCGACCGCAA 1439
AAAACTTGAT TGGGTGATG GTTCACGTAG TGGGCCATCG CCCTGATAGA CGGTTTTTCG 1499
CCCTTTGACG TTGGAGTCCA CGTTCTTTAA TAGTGGACTC TTGTTCCAAA CTGGAACAAC 1559
ACTCAACCCT ATCTCGGTCT ATTCTTTTGA TTTATAAGGG ATTTTGCCGA TTTCGGCCTA 1619
TTGGTTAAAA AATGAGCTGA TTTAACAAAT ATTAACGCG AATTTTAACA AAATATTAAC 1679
GTTTACAATT TCGCCTGATG CGGTATTTTC TCCTTACGCA TCTGTGCGGT ATTTCACACC 1739
GCATATGGTG CACTCTCAGT ACAATCTGCT CTGATGCCGC ATAGTTAAGC CAGCCCCGAC 1799
ACCCGCCAAC ACCCGCTGAC GCGCCCTGAC GGGCTTGTCT GCTCCCGGCA TCCGCTTACA 1859
GACAAGCTGT GACCGTCTCC GGGAGCTGCA TGTGTCAGAG GTTTTCACCG TCATCACCGA 1919
AACGCGCGAG ACGAAAGGGC CTCGTGATAC GCCTATTTTT ATAGGTTAAT GTCATGATAA 1979
TAATGGTTTC TTAGACGTCA GGTGGCACTT TTCGGGGAAA TGTGCGCGGA ACCCCTATTT 2039
GTTTATTTTT CTAAATACAT TCAAATATGT ATCCGCTCAT GAGACAATAA CCCTGATAAA 2099
TGCTTCAATA ATATTGAAAA AGGAAGAGTA TGAGTATTCA ACATTTCCGT GTCGCCCTTA 2159
TTCCCTTTTT TGCGGCATTT TGCCTTCCTG TTTTTGCTCA CCCAGAAACG CTGGTGAAAG 2219
TAAAAGATGC TGAAGATCAG TTGGGTGCAC GAGTGGGTTA CATCGAACTG GATCTCAACA 2279
GCGGTAAGAT CCTTGAGAGT TTTCGCCCCG AAGAACGTTT TCCAATGATG AGCACTTTTA 2339
AAGTTCTGCT ATGTCATACA CTATTATCCC GTATTGACGC CGGGCAAGAG CAACTCGGTC 2399
GCCGGGCGCG GTATTCTCAG AATGACTTGG TTGAGTACTC ACCAGTCACA GAAAAGCATC 2459
TTACGGATGG CATGACAGTA AGAGAATTAT GCAGTGCTGC CATAACCATG AGTGATAACA 2519
CTGCGGCCAA CTTACTTCTG ACAACGATCG GAGGACCGAA GGAGCTAACC GCTTTTTGC 2579
ACAACATGGG GGATCATGTA ACTCGCCTTG ATCGTTGGGA ACCGGAGCTG AATGAAGCCA 2639
TACCAAACGA CGAGCGTGAC ACCACGATGC CTGTAGCAAT GCCAACAACG TTGCGCAAAC 2699
TATTAACTGG CGAACTACTT ACTCTAGCTT CCCGGCAACA ATTAATAGAC TGGATGGAGG 2759
CGGATAAAGT TGCAGGACCA CTTCTGCGCT CGGCCCTTCC GGCTGGCTGG TTTATTGCTG 2819
ATAAATCTGG AGCCGGTGAG CGTGGGTCTC GCGGTATCAT TGCAGCACTG GGGCCAGATG 2879
GTAAGCCCTC CCGTATCGTA GTTATCTACA CGACGGGGAG TCAGGCAACT ATGGATGAAC 2939
GAAATAGACA GATCGCTGAG ATAGGTGCCT CACTGATTAA GCATTGGTAA CTGTCAGACC 2999
```

-continued

```
AAGTTTACTC ATATATACTT TAGATTGATT TAAAACTTCA TTTTTAATTT AAAAGGATCT   3059

AGGTGAAGAT CCTTTTTGAT AATCTCATGA CCAAAATCCC TTAACGTGAG TTTTCGTTCC   3119

ACTGAGCGTC AGACCCCGTA GAAAAGATCA AAGGATCTTC TTGAGATCCT TTTTTTCTGC   3179

GCGTAATCTG CTGCTTGCAA ACAAAAAAAC CACCGCTACC AGCGGTGGTT TGTTTGCCGG   3239

ATCAAGAGCT ACCAACTCTT TTTCCGAAGG TAACTGGCTT CAGCAGAGCG CAGATACCAA   3299

ATACTGTCCT TCTAGTGTAG CCGTAGTTAG GCCACCACTT CAAGAACTCT GTAGCACCGC   3359

CTACATACCT CGCTCTGCTA ATCCTGTTAC CAGTGGCTGC TGCCAGTGGC GATAAGTCGT   3419

GTCTTACCGG GTTGGACTCA AGACGATAGT TACCGGATAA GGCGCAGCGG TCGGGCTGAA   3479

CGGGGGGTTC GTGCACACAG CCCAGCTTGG AGCGAACGAC CTACACCGAA CTGAGATACC   3539

TACAGCGTGA GCTATGAGAA AGCGCCACGC TTCCCGAAGG GAGAAAGGCG ACAGGTATC    3599

CGGTAAGCGG CAGGGTCGGA ACAGGAGAGC GCACGAGGGA GCTTCCAGGG GGAAACGCCT   3659

GGTATCTTTA TAGTCCTGTC GGGTTTCGCC ACCTCTGACT TGAGCGTCGA TTTTTGTGAT   3719

GCTCGTCAGG GGGGCGGAGC CTATCGAAAA ACGCCAGCAA CGCGGCCTTT TTACGGTTCC   3779

TGGCCTTTTG CTGGCCTTTT GCTCACATGT TCTTTCCTGC GTTATCCCCT GATTCTGTGG   3839

ATAACCGTAT TACCGCCTTT GAGTGAGCTG ATACCGCTCG CCGCAGCCGA ACGACCGAGC   3899

GCAGCGAGTC AGTGAGCGAG GAAGCGGAAG AGCGCCCAAT ACGCAAACCG CCTCTCCCCG   3959

CGCGTTGGCC GATTCATTAA TGCAG                                        3984
```

( 2 ) INFORMATION FOR SEQ ID NO:2:

( i ) SEQUENCE CHARACTERISTICS:
( A ) LENGTH: 314 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ala Ser Met Thr Gly Gly Gln Gln Met Gly Thr Asn Gln Gly Lys
 1               5                  10                  15

Gly Val Val Ala Ala Gly Asp Lys Leu Ala Leu Phe Leu Lys Val Phe
            20                  25                  30

Gly Gly Glu Val Leu Thr Ala Phe Ala Arg Thr Ser Val Thr Thr Ser
        35                  40                  45

Arg His Met Val Arg Ser Ile Ser Ser Gly Lys Ser Ala Gln Phe Pro
    50                  55                  60

Val Leu Gly Arg Thr Gln Ala Ala Tyr Leu Ala Pro Gly Glu Asn Leu
65                  70                  75                  80

Asp Asp Lys Arg Lys Asp Ile Lys His Thr Glu Lys Val Ile Thr Ile
                85                  90                  95

Asp Gly Leu Leu Thr Ala Asp Val Leu Ile Tyr Asp Ile Glu Asp Ala
            100                 105                 110

Met Asn His Tyr Asp Val Arg Ser Glu Tyr Thr Ser Gln Leu Gly Glu
        115                 120                 125

Ser Leu Ala Met Ala Ala Asp Gly Ala Val Leu Ala Glu Ile Ala Gly
    130                 135                 140

Leu Cys Asn Val Glu Ser Lys Tyr Asn Glu Asn Ile Glu Gly Leu Gly
145                 150                 155                 160

Thr Ala Thr Val Ile Glu Thr Thr Gln Asn Lys Ala Ala Leu Thr Asp
                165                 170                 175
```

| | | | | | | | | | | | | | | | |
|---|---|---|---|---|---|---|---|---|---|---|---|---|---|---|---|
|Gln|Val|Ala|Leu<br>180|Gly|Lys|Glu|Ile|Ile<br>185|Ala|Ala|Leu|Thr|Lys<br>190|Ala|Arg|
|Ala|Ala|Leu<br>195|Thr|Lys|Asn|Tyr|Val<br>200|Pro|Ala|Ala|Asp|Arg<br>205|Val|Phe|Tyr|
|Cys|Asp<br>210|Pro|Asp|Ser|Tyr|Ser<br>215|Ala|Ile|Leu|Ala|Ala<br>220|Leu|Met|Pro|Asn|
|Ala<br>225|Ala|Asn|Tyr|Ala|Ala<br>230|Leu|Ile|Asp|Pro|Glu<br>235|Lys|Gly|Ser|Ile|Arg<br>240|
|Asn|Val|Met|Gly|Phe<br>245|Glu|Val|Val|Glu|Val<br>250|Pro|His|Leu|Thr|Ala<br>255|Gly|
|Gly|Ala|Gly|Thr<br>260|Ala|Asp|Ser|Ser|Leu<br>265|Val|Pro|Ser|Ser|Asp<br>270|Pro|Leu|
|Val|Thr|Ala<br>275|Ala|Ser|Val|Leu|Glu<br>280|Phe|Cys|Arg|Tyr|Pro<br>285|Ser|His|Trp|
|Arg|Pro<br>290|Leu|Glu|Gln|Ile|Arg<br>295|Leu|Leu|Thr|Lys|Pro<br>300|Glu|Arg|Lys|Leu|
|Ser<br>305|Trp|Leu|Leu|Pro|Pro<br>310|Leu|Ser|Asn|Asn| | | | | | |

We claim:

1. A method for mapping the ligand binding domains of a protein which binds to a ligand, the method comprising the steps of (a) randomly cleaving the gene encoding for the protein into DNA fragments of sufficient length so as to likely include the ligand binding domain;

(b) enzymatically adding only a single nucleotide residue overhang to one end of each strand of the DNA fragments from step (a);

(c) inserting the DNA fragments from step (b) into a recombinant DNA construct having regulatory elements sufficient to transcribe and translate inserted DNA fragments in a host, the DNA construct having been prepared with single nucleotide overhangs complementary to the single nucleotide overhangs on the fragments from step (b);

(d) transforming the DNA construct from step (c) into a host which transcribes and translates the recombinant DNA construct and culturing the host under conditions so that the DNA construct expresses peptides encoded by the DNA fragments;

(e) screening the peptides for a peptide which binds to the ligand;

(f) sequencing the DNA fragment which expresses the peptide which binds to the ligand; and (g) determining the corresponding amino acid sequence encoded by the DNA fragment of step (f), to thereby map the ligand binding domain of the protein.

2. A method as claimed in claim 1 wherein in step (b) a single dA nucleotide is the overhang.

3. A method as claimed in claim 2 wherein the single dA nucleotide is added by reaction of the DNA fragments with Tth DNA polymerase with excess dATP present.

4. A method as claimed in claim 1 wherein step (a) is performed by digestion of the gene with DNase I.

5. A method as claimed in claim 1 wherein step (e) uses as the ligand an antibody which binds to the protein, and the ligand binding domain is the epitope to which the antibody binds.

6. A method as claimed in claim 1 wherein the DNA construct is prepared in step (c) by digestion with a restriction enzyme which cleaves the DNA construct to leave the single nucleotide overhang.

7. A method for mapping the ligand binding domains of a protein which binds to a ligand, the method comprising the steps of (a) randomly cleaving the gene encoding for the protein into DNA fragments of sufficient length so as to likely include the ligand binding domain;

(b) enzymatically adding only a single A nucleotide residue overhang to the 3' end of each strand of the DNA fragments from step (a), wherein the enzymatic addition is made using Tth DNA polymerase;

(c) inserting the DNA fragments from step (b) into a recombinant DNA construct having regulatory elements sufficient to transcribe and translate inserted DNA fragments in a host, the DNA construct having been prepared with single nucleotide overhangs complementary to the single nucleotide overhangs on the fragments from step (b);

(d) transforming the DNA construct from step (c) into a host which transcribes and translates the recombinant DNA construct and culturing the host under conditions so that the DNA construct expresses peptides encoded by the DNA fragments;

(e) screening the peptides for a peptide which binds to the ligand;

(f) sequencing the DNA fragment which expresses the peptide which binds to the ligand; and (g) determining the corresponding amino acid sequence encoded by the DNA fragment of step (f), to thereby map the ligand binding domain of the protein.

8. A method as claimed in claim 7 where step (a) is performed by digestion of the gene with DNase I.

9. A method as claimed in claim 7 wherein step (e) uses as the ligand an antibody which binds to the protein, and the ligand binding domain is the epitope to which the antibody binds.

10. A method as claimed in claim 7 wherein the DNA construct is prepared in step (c) by digestion with a restriction enzyme which cleaves the DNA construct to leave the single nucleotide overhang.

* * * * *